United States Patent [19]

Liang et al.

[11] Patent Number: 6,077,981
[45] Date of Patent: Jun. 20, 2000

[54] PROCESS FOR THE PRODUCTION OF CYCLOPROPYLMETHYL HALIDES

[75] Inventors: Shaowo Liang, Kingsport, Tenn.; Colin Henry Ridyard, Pentraeth, United Kingdom; Daniel Latham Terrill, Kingsport, Tenn.; Clyde Neil Clubb, Longview, Tex.

[73] Assignee: Eastman Chemical Company, Kingsport, Tenn.

[21] Appl. No.: 09/143,224

[22] Filed: Aug. 28, 1998

[51] Int. Cl.$^7$ .................................................. C07C 17/16
[52] U.S. Cl. ............................................ 570/142; 570/258
[58] Field of Search ...................... 570/142, 258

[56] References Cited

U.S. PATENT DOCUMENTS

| | | |
|---|---|---|
| 2,153,170 | 4/1939 | Buc et al. . |
| 3,385,857 | 5/1968 | Mizzoni et al. . |
| 4,739,057 | 4/1988 | Leone-Bay et al. ................... 544/334 |
| 4,863,918 | 9/1989 | Gala et al. . |
| 5,138,110 | 8/1992 | Segall et al. ........................... 570/258 |
| 5,288,932 | 2/1994 | Kaufhold . |
| 5,475,151 | 12/1995 | Liang et al. . |
| 5,502,257 | 3/1996 | Liang et al. . |
| 5,905,176 | 5/1999 | Liang .................................... 570/214 |

FOREIGN PATENT DOCUMENTS

| | | |
|---|---|---|
| 0380312 A1 | 8/1990 | European Pat. Off. . |
| 10-167999 | 6/1998 | Japan . |
| 539110 | 12/1984 | Spain . |
| 279821 | 3/1994 | Switzerland . |
| WO-9304047 | 3/1993 | WIPO . |
| WO-97/30958 | 8/1997 | WIPO . |

OTHER PUBLICATIONS

Journal of Medical Chemistry—Chim. Therap., vol. 15, 571 (1972).

Lee et al, Can. J. Chem., 1980, vol. 58, 1980, 1075–1079.

*Primary Examiner*—Johann Richter
*Assistant Examiner*—Sonya Wright
*Attorney, Agent, or Firm*—Michael J. Blake; Harry J. Gwinnell

[57] ABSTRACT

Disclosed is a process for the production of cyclopropylmethyl halides (CPMX) such as cyclopropylmethyl chloride (CPMCl) and cyclopropylmethyl bromide (CPMBr) wherein cyclopropanemethanol (CPMO) is contacted with an aqueous solution of a hydrogen halide (HX) at a temperature in the range of −30° C. to 35° C. Also disclosed is a three-step process wherein CPMO is converted to a CPMX, the CPMX is separated as a liquid organic phase from the aqueous hydrogen halide by decantation and then is subjected to fractional distillation to provide CPMX in high purity. Finally, a process for the co-production of a CPMX and a cyclobutyl halide (CBX) is disclosed.

4 Claims, No Drawings

PROCESS FOR THE PRODUCTION OF CYCLOPROPYLMETHYL HALIDES

This invention pertains to a process for the production of cyclopropylmethyl halides (CPMX) such as cyclopropylmethyl chloride (CPMCl) and cyclopropylmethyl bromide (CPMBr). The process involves treatment of cyclopropanemethanol (CPMO) with an aqueous solution of a hydrogen halide (HX) at a temperature in the range of −30° C. to 35° C. Another embodiment of the invention involves a three-step process wherein CPMO is converted to a CPMX, the CPMX is separated from the aqueous hydrogen halide by decantation and then is subjected to fractional distillation to provide CPMX in high purity. Another embodiment of the present invention provides a process for the co-production of a CPMX and a cyclobutyl halide (CBX).

The preparation of cyclopropylmethyl halides by reacting CPMO with a phosphorus trihalide is described in *J. Med. Chem.-Chim. Therap.* 15, 571 (1980). The disclosed process requires very low temperatures, e.g. −65° to −80° C., in order to obtain acceptable selectivity to the desired CPMX. U.S. Pat. No. 3,385,857 describes a similar method for the preparation of CPMBr using diethyl ether as a solvent in order to achieve better recovery of the product. Again, the temperature was −78° C. Published PCT Patent Application WO-97/30958 describes a process for the production of CPMX by reacting CPMO with excess chlorine or bromine in the presence of triphenylphosphine and dimethyl formamide solvent. In order to obtain the desired products in high purity, large amounts of triphenylphosphine are required for the process. Also, the reaction is carried out under very dilute condition requiring the use of a large amount of dimethyl formamide. The process of WO-97/30958 therefore results in poor throughput and the generation of large amounts of waste materials which make this process unattractive for commercial-scale production of CPMX.

U.S Pat. No. 5,288,932 describes a process by a so-called one-pot, two-step process in which CPMO is reacted with methanesulfonic acid halides to form mesylates in the presence of trialkylamines. The mesylates are decomposed thermally in the presence of the amine hydrohalide salts to generate the CPMX along with large amounts of aminesulfonic acid salts. Such formation of large amounts of salts makes product isolation difficult and presents disposal and environmental problems. The process also requires a complicated and costly measurement and temperature control technique and presents difficulties of operating on a commercial scale. Lee at al, *Can. J. Chem.*, 1980, 58, 1075–79 discloses the reaction of CPMO with dilute, i.e., up to 2.0 Normal, aqueous hydrochloric acid at 60 or 85° C. for 1.5 to 10 hours. The reaction gave 10 to 13 products with cyclobutanol as the major product. Only trace amounts CPMCl were observed.

We have developed a simple and efficient process of the production of CPMX. One embodiment of the invention provides a process for the production of CPMX by contacting CPMO with an aqueous HX solution at a temperature of −30° to 35° C. The crude product obtained from the process comprises mainly CPMX along with cyclobutyl halide (CBX) and trace amounts of 4-halo-1-butene. The hydrohalide HX preferably is hydrogen bromide or, especially, hydrogen chloride. The initial reaction of CPMO and HX results in the formation of a two-phase liquid system comprising an organic phase comprising the halide products and an aqueous phase comprising the aqueous HX solution. The crude product thus can be recovered by decantation. Distillation of the product mixture, preferably in the presence of an acid scavenger or acceptor, gives CPMX having a purity satisfactory for use in other organic syntheses processes, e.g. a purity of 95% or greater. The concurrent addition of an acid scavenger during the distillation effectively prevents or minimizes decomposition of the desired CPMX product from prolonged heating, especially when the distillation column contain a metal, e.g., steel, packing material.

Thus, a second embodiment of the present invention provides a process for the production of CPMX having a purity of 95% or greater, preferably 97% or greater, which comprises the steps of:

(1) contacting CPMO with an aqueous HX solution at a temperature of −30° to 35° C. to obtain a reaction mixture comprising (i) an organic phase comprising CPMX, CBX and 4-halo-1-butene and (ii) an aqueous phase comprising the aqueous HX solution;

(2) separating organic phase (i) from aqueous phase (ii) from step (1) by decantation; and (3) subjecting organic phase (i) to fractional distillation wherein organic phase (i) is fed to the mid-section of a distillation column operated at a temperature and pressure to provide (i) a column overhead vapor stream comprising a CBX and 4-halo-1-butene and (ii) a column base vapor stream comprising CPMX.

The process of the present invention co-produces CPMX and CBX in CPMX:CBX mole ratios in the range of about 10:1 to 0.5:1, depending upon the conditions, particularly the temperature, of the process. Thus, a third embodiment of the present invention is the co-production of a CPMX and CBX in CPMX:CBX mole ratios in the range of about 10:1 to 0.5:1 by contacting CPMO with an aqueous HX solution at a temperature of −30° to 35° C. Cyclopropylmethyl halides and cyclobutyl halides are useful intermediates for the production of pharmaceuticals. See, for example, Published PCT Patent Application WO 9304047, Spanish Patent ES 539110, U.S. Pat. No. 4,863,918, Czech Patent CZ 279821 and European Patent Publication EP 0380312 A1.

In the first embodiment of our invention, a CPMX is produced by contacting CPMO with an aqueous HX solution at a temperature of −30° to 35° C. wherein X is a halogen atom, preferably Cl or Br, most preferably Cl. The concentration of the aqueous HX solution may be in the range of about 20 to 80 weight percent HX, preferably about 30 to 60 weight percent HX. Higher HX concentrations can be achieved or maintained by continuously introducing HX gas into the reaction zone of the process. The temperature at which the first embodiment is performed may be in the range of −30° to 35° C. but preferably is in the range of about −15 to 20° C. and most preferably in the range of about −10 to 5° C. The crude product comprising CPMX and CBX with smaller amounts of 4-halo-1-butene forms a liquid organic phase which separates from the aqueous HX solution and may be recovered using conventional decantation procedures and equipment. Since CPMO is completely soluble in the aqueous HX solution and the halide products are insoluble in the aqueous phase, the separation of the product (organic phase) may be accomplished by simple decanting. Such differences of solubility between starting material CPMO and product halides in the aqueous HX solution is advantageous for commercial operations since the CPMX formed exists the organic layer while the unreacted CPMO remains in the aqueous layer. Thus, the reaction may be driven to completion while avoiding decomposition and/or isomerization of the CPMX product by prolonged contact with the acid.

The second embodiment of the invention provides a process for the production of CPMX having a purity of 95% or greater, preferably 97% or greater, which comprises the steps of:

(1) contacting CPMO with an aqueous HX solution at a temperature of −30° to 35° C. to obtain a reaction mixture comprising (i) an organic phase comprising CPMX, CBX and 4-halo-1-butene and (ii) an aqueous phase comprising the aqueous HX solution;

(2) separating organic phase (i) from aqueous phase (ii) from step (1) by decantation; and (3) subjecting organic phase (i) to fractional distillation wherein organic phase (i) is fed to the mid-section of a distillation column operated at a temperature and pressure to provide (i) a column overhead vapor stream, i.e., a vapor stream removed from the upper section or top of the distillation column, comprising a CBX and 4-halo-1-butene and (ii) a column base vapor stream, i.e., a vapor stream removed from the lower section or bottom of the distillation column, comprising CPMX.

Steps (1) and (2) of the three-step embodiment of the invention are carried out according to the procedures described above. The distillation column of step (3) typically is operated at a pressure of 100 Torr up to a pressure moderately above ambient pressure, e.g., up to about 2 to 3 bar absolute, and a column base temperature of about 30 to 115° C. For example, when the distillation is carried out at approximately ambient pressure, the column base temperature normally will be in the range of 80 to 115° C. and an overhead vapor take-off temperature of 70 to 84° C. To achieve good separation of the CPMX, CBX and 4-halo-1-butene which have similar boiling points, (CPMCl=86° C., CBCl=83° C., 4-chloro-1-butene=75° C. at ambient pressure), a substantial portion of the overhead vapor is condensed and returned to the upper section of the column as reflux. Reflux ratios of about 10:1 to 50:1 with 40 to 60 theoretical plates typically are required to achieve the desired separation.

Heating the CPMX product in the presence of an acid can cause significant decomposition and/or isomerization of the product. Such catalytic amounts of acid can be generated as a result of the product halide contacting the materials of construction of the equipment, e.g., stainless steels, used for distillation. This acid-catalyzed decomposition/isomerization may be substantially overcome by performing the distillation in the presence of an acid scavenger or acceptor. This may be accomplished by the concurrent addition of an acid scavenger to the column during the distillation. Examples of acid scavengers which may be employed in the distillation include organic amines such as trialkylamines, pyridine and the likes), amides such as N-methylpyrrolidone and N-cyclohexylpyrrolidone, and/or inorganic bases such as sodium or potassium bicarbonate, sodium or potassium carbonates, and carboxylate salts of strong bases e.g., sodium acetate. The preferred acid scavengers are the trialkylamines having boiling points greater than the boiling point of any of the components of the crude product being distilled, e.g., trialkylamines having boiling points of about 100 to 250° C. at ambient pressure. The amount of acid scavenger typically required gives an acid scavenger:crude product weight ratio in the range of about 0.001:1 to 0.1:1.

Distillation step (3) is carried out by feeding the crude CPMX, i.e., organic phase (i) from step (2), to the mid-section of a distillation column operated at a temperature and pressure which provides a column overhead vapor stream comprising a CBX and 4-halo-1-butene and a column base vapor stream comprising CPMX. The distillation preferably is carried out while concurrently feeding an acid scavenger to the upper section of the distillation column. Operation of the distillation in a continuous manner has the advantage of limiting the heating time of the CPMX to minimize the possible thermal decomposition. The preferred acid scavenger having a higher boiling point remains in the base of the distillation set.

The other effective way to reduce the isomerization during the distillation is to carry out the distillation under reduced pressure which allows the distillation to be carried out at lower temperature 30–50° C. and to avoid the corrosion problems. The use of equipment such as glass column with packing, which is free of corrosion concerns, for the distillation of crude product can also effectively prevent the isomerization.

The processes of this invention may be carried out in a continuous mode of operation. For example, CPMO may be introduced continuously into the lower part of a reaction zone wherein CPMO is halogenated by contact with an aqueous HX solution. The crude products which forms as an organic layer may be separated from the upper part of the reaction zone. HX gas is continuously introduced into the lower part of the reaction zone to maintain the concentration of the hydrogen halide solution constant. The advantage of continuous operation is to minimize the contact time of the product CPMX with the acid to avoid the further isomerization of CPMX to its isomers.

The CPMO utilized in the present invention is readily obtained by the hydrogenation of cyclopropanecarboxaldehyde (CPCA) in the presence of a cobalt or nickel catalyst according to the process described in U.S. Pat. No. 5,475,151. The CPCA may be produced by the thermal isomerization of 2,3-dihydrofuran as is described in U.S. Pat. No. 5,502,257.

The processes provided by the present invention are further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic spectrometry and gas chromatography-mass spectrometry by comparison to authentic samples. The percentages specified in the examples are by weight unless otherwise specified.

EXAMPLE 1

To a 2-liter, jacketed flask was placed 36% hydrochloric acid (1577 g, 16 mol, 1 liter) and cooled to 3° C. CPMO (289.9 g, 4 mol, 99% purity) was added over a period of 1 hour while maintaining the temperature at 3° C. The reaction mixture was allowed to stand at this temperature for 16 hours. An organic phase which formed was separated to give 337.84 g of crude product which comprised 60.48% CPMCl, 35.28% CBCl and 4.24% 4-chloro-1-butene.

Distillation of the crude CPMCl was carried out in a column with stainless steel structure packing with about 50 theoretical plates and a reflux ratio of 30:1. The crude product was fed continuously to the middle section of the column while tributylamine was fed at the top of the column. Pure CPMCl was continuously removed as the base vapor after rectification with a short column section packed with Berl saddles. CPMCl was obtained in a purity of 97% assay and with 90% recovery.

EXAMPLE 2

36% Hydrochloric acid (1.4 liters) was cooled to −5° C. and CPMO (288 g, 3.88 mol) was added while maintaining the temperature below 0° C. The reaction mixture was stirred for 3.5 hours at about −5° C. and left to stand for 16 hours at −5 to 0° C. The organic phase (top layer) was separated and washed with water to give 290 g crude product comprised of 61.5% CPMCl, 35.6% CBCl and 2.9% 4-chloro-1-butene.

EXAMPLE 3

36% Hydrochloric acid (1.4 liters) was cooled to 10° C. and CPMO (288 g, 3.88 mol) was added while maintaining the temperature at 9–11° C. The reaction mixture was stirred for 3.5 hours at about 10° C. The organic phase (top layer) was separated and washed with water to give 282 g crude product comprised of 60.6% CPMCl, 35.8% CBCl and 3.6% 4-chloro-1-butene.

EXAMPLE 4

36% Hydrochloric acid (1.4 liters) was cooled to 20° C. and CPMO (288 g, 3.88 mol) was added while maintaining the temperature 19–21° C. The reaction mixture was stirred for 3.5 hours at about 20° C. The organic phase (top layer) was separated and washed with water to give 273 g crude product comprised of 58.9% CPMCl, 36.8% CBCl and 4.3% 4-chloro-1-butene.

EXAMPLE 5

28% Hydrochloric acid (1.4 liters) was cooled to −5° C. and CPMO (288 g, 3.88 mol) was added while maintaining the temperature below 0° C. The reaction mixture was stirred for 3.5 hours at about −5° C. and left to stand for 16 hours at −5 to 0° C. The organic phase (top layer) was separated and washed with water to give 193 g crude product comprise of 54.7% CPMCl, 40.5% CBCl and 4.8% 4-chloro-1-butene.

EXAMPLE 6

To a 2-liter jacketed flask was placed 48% hydrobromic acid (1490 g, 8.83 mol, 1 liter) and the mixture was cooled to 3° C. CPMO (151.62 g, 2.085 mol, 99% purity) was added over a period of 30 minutes while maintaining the temperature at 3° C. The reaction mixture was allowed to stand at 3° C. for 24 hours. The organic phase was drained off to give 268.83 g of crude product comprised of 51.86% CPMBr, 35% CBBr and 8.33% 4-bromo-1-butene.

The crude product was distilled using a Teflon spinning band distillation system to give about 90% recovery of CPMBr having a purity of 98%. Small amounts (1% by weight of the total crude product) of N-methylpyrrolidone was added to the base of the distillation system to prevent the decomposition of CPMBr during the distillation.

EXAMPLE 7

48% Hydrobromic acid (1.4 liters) was cooled to −5° C. and CPMO (300 g, 4.04 mol) was added while maintaining the temperature below 0° C. The reaction mixture was stirred for 3.5 hours at about −5° C. and left to stand for 16 hours at −5 to 0° C. The organic phase (bottom layer) was separated and washed with water to give 256 g crude product which comprises 59% CPMBr, 37% CBBr and 4% 4-bromo-1-butene.

EXAMPLE 8

62% Hydrochloric acid (0.25 liters) was cooled to −5° C. and CPMO (50 g, 0.67 mol) was added while maintaining the temperature below 0° C. The reaction mixture was stirred for 3.5 hours at about 0° C. and allowed to stand for 16 hours at −5 to 0° C. The organic phase (top layer) was separated and washed with water to give 71 g crude product comprised of 54% CPMBr, 37% CBBr and 7% 4-bromo-1-butene.

The invention has been described in detail with particular reference to preferred embodiments thereof, but it will be understood that variations and modifications can be effected within the spirit and scope of the invention.

We claim:

1. Process for the production of cyclopropylmethyl halide (CPMX) which comprises the steps of:

(1) contacting cyclopropanemethanol with an aqueous solution of a hydrogen halide at a temperature of −30° to 35° C. to obtain a reaction mixture comprising (i) an organic phase comprising CPMX, a cyclobutyl halide (CBX) and 4-halo-1-butene and (ii) an aqueous phase comprising the aqueous hydrogen halide solution;

(2) separating organic phase (i) from aqueous phase (ii) from step (1) by decantation; and (3) subjecting organic phase (i) to fractional distillation wherein organic phase (i) is fed to the mid-section of a distillation column operated at a temperature and pressure to provide (i) a column overhead vapor stream comprising a CBX and 4-halo-1-butene and (ii) a column base vapor stream comprising CPMX.

2. Process according to claim 1 wherein in step (1) the hydrogen halide is hydrogen chloride or hydrogen bromide and the concentration of the hydrogen halide in the aqueous solution is about 20 to 80 weight percent and step (3) is carried out in the presence of an acid scavenger.

3. Process according to claim 2 wherein step (1) is carried out at a temperature in the range of about −15 to 20° C. and step (3) is carried out at ambient pressure using a column base temperature of about 80 to 115° C. and in the presence of a trialkylamine having a boiling point of about 100 to 250° C.

4. Process according to claim 3 wherein step (1) is carried out at a temperature in the range of about −10 to 5° C. using a 30 to 60 weight percent aqueous solution of hydrogen chloride to obtain a reaction mixture comprising (i) an organic phase comprising cyclopropylmethyl chloride, cyclobutyl chloride and 4-chloro-1-butene and (ii) an aqueous phase comprising the aqueous hydrogen chloride solution; step (3) is carried out using tributylamine as the acid scavenger.

* * * * *